United States Patent
Verhoef et al.

(10) Patent No.: US 12,000,848 B2
(45) Date of Patent: Jun. 4, 2024

(54) INCUBATION SYSTEM AND METHOD FOR AUTOMATED CELL CULTURE AND TESTING

(71) Applicant: Molecular Devices, LLC, San Jose, CA (US)

(72) Inventors: Martin Verhoef, Redwood, CA (US); Josef J. Atzler, Hallein (AT); Andreas Kenda, Klagenfurt (AT)

(73) Assignee: Molecular Devices, LLC, San Jose, CA (US)

( * ) Notice: Subject to any disclaimer, the term of this patent is extended or adjusted under 35 U.S.C. 154(b) by 1033 days.

(21) Appl. No.: 16/377,395

(22) Filed: Apr. 8, 2019

(65) Prior Publication Data

US 2020/0319217 A1    Oct. 8, 2020

(51) Int. Cl.
*G01N 35/00* (2006.01)
*C12M 1/00* (2006.01)
(Continued)

(52) U.S. Cl.
CPC ......... *G01N 35/0099* (2013.01); *C12M 1/005* (2013.01); *C12M 1/268* (2013.01);
(Continued)

(58) Field of Classification Search
CPC ......... G01N 35/0099; G01N 35/00871; G01N 35/1072; G01N 2035/00425;
(Continued)

(56) References Cited

U.S. PATENT DOCUMENTS 9,715,099 B2    7/2017  Ozcan et al.
2004/0147012 A1  7/2004  Yokoi
(Continued)

FOREIGN PATENT DOCUMENTS

CN      1656210 A       8/2005
CN    107828654 A  *    3/2018   ............ C12M 23/12
(Continued)

OTHER PUBLICATIONS

Translation of JP-2018516591-A, Jun. 28, 2018.*
(Continued)

*Primary Examiner* — Benjamin R Whatley
(74) *Attorney, Agent, or Firm* — Merchant & Gould P.C.

(57) ABSTRACT

Incubation system and method for automated cell culture and/or testing. An exemplary incubation system may comprise a housing forming a chamber. A rack may define storage positions to support an array of sample holders inside the chamber. A detection robot may be configured to capture one or more images of cells contained by one or more wells of each sample holder while the sample holder remains at one of the storage positions of the rack. A fluid handling station may be configured to add fluid to, and/or remove fluid from, one or more wells of each of the sample holders inside the housing. At least one plate robot may be configured to move sample holders between the rack and the fluid handling station. A computer may control operation of the detection robot, the fluid handling station, and the at least one plate robot.

15 Claims, 7 Drawing Sheets

(51) Int. Cl.
*C12M 1/26* (2006.01)
*C12M 1/32* (2006.01)
*C12M 1/34* (2006.01)
*C12M 3/00* (2006.01)
*C12Q 1/02* (2006.01)
*G01N 35/10* (2006.01)
*G06V 20/69* (2022.01)
*H04N 7/18* (2006.01)

(52) U.S. Cl.
CPC ............ *C12M 23/12* (2013.01); *C12M 23/48* (2013.01); *C12M 41/12* (2013.01); *C12M 41/14* (2013.01); *C12Q 1/02* (2013.01); *G01N 35/00871* (2013.01); *G01N 35/1072* (2013.01); *G06V 20/693* (2022.01); *H04N 7/183* (2013.01); *G01N 2035/00356* (2013.01); *G01N 2035/00425* (2013.01); *G01N 2035/103* (2013.01)

(58) Field of Classification Search
CPC ........... G01N 2035/103; G06V 20/693; C12M 23/12; C12M 23/48; C12M 1/005; C12M 41/14; C12Q 1/02; H04N 7/183
See application file for complete search history.

(56) References Cited

U.S. PATENT DOCUMENTS

| | | | |
|---|---|---|---|
| 2006/0110287 A1 | 5/2006 | Kraemer et al. | |
| 2006/0210435 A1* | 9/2006 | Alavie | G01N 35/0092 422/65 |
| 2009/0325280 A1* | 12/2009 | Osawa | C12M 23/48 435/288.7 |
| 2014/0300696 A1* | 10/2014 | Ozcan | G02B 21/365 348/40 |
| 2016/0122794 A1 | 5/2016 | Trenholm et al. | |
| 2017/0023535 A1* | 1/2017 | Stanley | G01N 1/405 |
| 2018/0011443 A1 | 1/2018 | Stahl et al. | |
| 2018/0087020 A1* | 3/2018 | Blanchard | C12M 33/00 |
| 2018/0346868 A1 | 12/2018 | Blanchard | |
| 2019/0024036 A1* | 1/2019 | Hitomi | C12M 41/48 |
| 2019/0106670 A1* | 4/2019 | Vacic | C12M 41/14 |
| 2021/0215727 A1* | 7/2021 | Ueda | G02B 21/26 |

FOREIGN PATENT DOCUMENTS

| | | | | |
|---|---|---|---|---|
| JP | 2004-166558 A | | 6/2004 | |
| JP | 2005-323509 A | | 11/2005 | |
| JP | 2009-525756 A | | 7/2009 | |
| JP | 2009-296938 A | | 11/2010 | |
| JP | 2014-526687 A | | 10/2014 | |
| JP | 2018516591 A | * | 6/2018 | ............ C12M 23/50 |
| WO | 2014/033889 | | 3/2014 | |
| WO | 2018/179081 | | 10/2018 | |

OTHER PUBLICATIONS

PCT International Search Report and Written Opinion in Application PCT/US2020/027990, dated Jun. 25, 2020, 12 pages.
PCT International Preliminary Report on Patentability in Application PCT/US2020/027990, dated Oct. 21, 2021, 9 pages.
European Extended Search Report in Application 20787847.1, dated May 17, 2023, 7 pages.
Chinese Office Action in Application 2020800431190, dated Jul. 29, 2023, 13 pages.
Japanese Notice of Refusal and Search Report in Application 2021-559432, mailed Mar. 18, 2024, 45 pages.

* cited by examiner

INCUBATION SYSTEM AND METHOD FOR AUTOMATED CELL CULTURE AND TESTING

INTRODUCTION

A typical incubator for cell culture is little more than a temperature-controlled box, often with the ability to regulate the level of carbon dioxide. The box forms a humidified incubation chamber to hold culture vessels containing cells. To gain access to the culture vessels and the cells therein for any purpose, such as viewing, feeding, or splitting, the incubation chamber must be opened to the ambient environment. However, opening the chamber reduces the stability of its climate and increases the likelihood of contamination. Moreover, a user must be physically present for manipulation of cell cultures, which can necessitate trips to the laboratory at night and on weekends. Improved incubators for cell culture are needed.

SUMMARY

The present disclosure provides an incubation system and method for automated cell culture and/or testing. An exemplary incubation system, also referred to as an incubator, may comprise a housing forming a chamber. A rack may define storage positions to support an array of sample holders (e.g., microplates) inside the chamber. A detection robot may be configured to capture one or more images of cells contained by one or more wells of each sample holder while the sample holder remains at one of the storage positions of the rack. A fluid handling station may be configured to add fluid to, and/or remove fluid from, one or more wells of each of the sample holders inside the housing. At least one plate robot may be configured to move sample holders between the rack and the fluid handling station. A computer may control operation of the detection robot, the fluid handling station, and the at least one plate robot.

DETAILED DESCRIPTION

Figure 1:
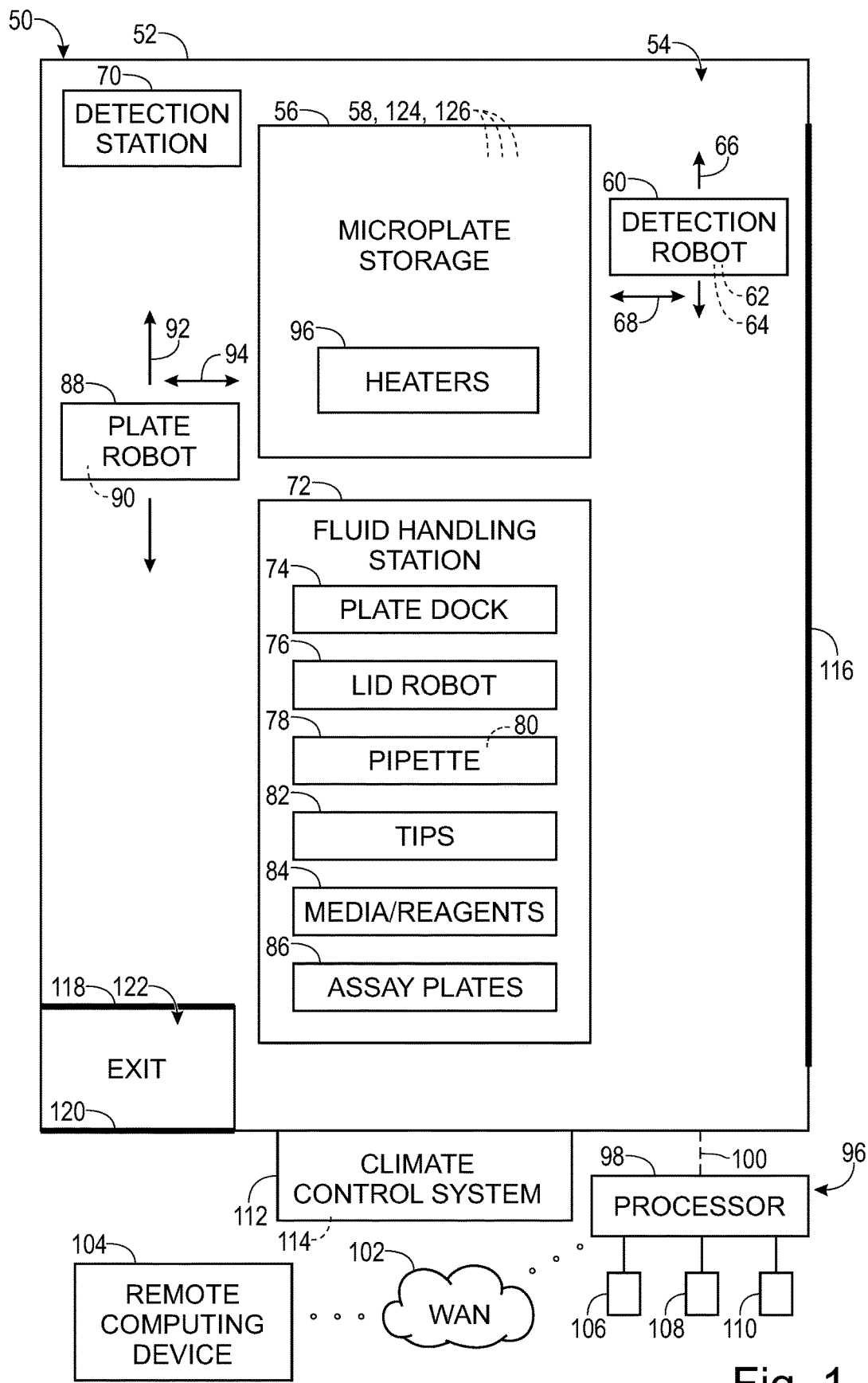
FIG. 1 is a schematic top view an exemplary smart incubator for culturing and/or testing biological cells, wherein the smart incubator has a shared chamber for storage of sample holders and handling of fluid, in accordance with aspects of the present disclosure.

The present disclosure provides an incubation system and method for automated cell culture and/or testing. An exemplary incubation system may comprise a housing forming a chamber. A rack may define storage positions to support an array of sample holders (e.g., microplates) inside the chamber. A detection robot may be configured to capture one or more images of cells contained by one or more wells of each sample holder while the sample holder remains at one of the storage positions of the rack. A fluid handling station may be configured to add fluid to, and/or remove fluid from, one or more wells of each of the sample holders inside the housing. At least one plate robot may be configured to move sample holders between the rack and the fluid handling station. A computer may control operation of the detection robot, the fluid handling station, and the at least one plate robot.

An exemplary method of automated cell culture and/or testing is provided. In the method, one or more images may be captured of cells contained in one or more wells of each sample holder of a plurality of sample holders. The plurality of sample holders may be stored at storage positions defined by a rack inside an incubator. The sample holder may remain in its storage position in the rack as the one or more images are captured for the sample holder. The sample holder may be moved from the rack to a fluid handling station inside the incubator using a plate robot. Fluid may be removed from and/or added to at least one well of the sample holder at the fluid handling station.

The current state of the art in incubators does not include any built-in intelligence and/or decision-making tools or attributes. Moreover, incubators are not remote-controlled, and cells in an incubator cannot be followed to check for viability or the need for media replacement, addition of test compounds, or any other step a user may have to perform.

The incubator of the present disclosure may enable automated short-term and long-term culture in sample holders, such as microplates, to allow monitoring of multiple parameters over the time-course of cultivation. A controlling computer may automatically take action, or alert lab personnel, if data collected by one or more sensors of the incubator meet one or more predefined criteria. For example, the computer may feed cells (e.g., change the growth medium), split cells, add a test compound(s) to cells, create assay mixtures, or the like, if captured images of cell cultures indicate an action is needed, or may notify one or more lab personnel (i.e., users) of a situation needing attention. The incubator can automate cell culture, improve the health of cells, and provide better in situ experimentation all by better knowledge of cell health and cell growth.

The smart incubators disclosed herein may be used for any suitable purpose. They can reduce labor and optimize workflow for assay development and compound testing. Clonal populations of cells may be cultured, fed, and assayed. Organ-on-chip cultures may be cultivated and tested in non-microplate settings. Mini-bioreactors may provide cell line development, with mixing of cells and media added.

Further aspects of the present disclosure are described in the following sections: (I) definitions, (II) overview of smart incubators, (III) methods of sample incubation and processing, and (IV) examples.

I. Definitions

Technical terms used in this disclosure have meanings that are commonly recognized by those skilled in the art. However, the following terms may be further defined as described below.

Chemical sensor—a device and/or a compound (e.g., a sensor dye) that detects or measures the concentration of a chemical analyte, such as free protons (for pH), oxygen, carbon dioxide, or the like. The chemical sensor may have an optical property that is sensitive to the concentration of the chemical analyte. The optical property may include photoluminescence intensity, photoluminescence lifetime, photoluminescence polarization, photoluminescence quenching/energy transfer, chemiluminescence intensity, absorbance, or the like. The optical property of the chemical sensor may be read using an optical sensor, with or without illumination using an associated light source, to measure the concentration of the chemical analyte. In some embodiments, the device may include a chemical sensor compound that is trapped in a matrix, to localize the sensor compound within a larger fluid volume (e.g., a volume of culture medium in a microplate well). The matrix may be attachable to a surface, such as with an adhesive. The surface may be an inside surface of a well, and the optical property may be detected through a wall of the well.

Computer—an electronic device for storing and processing data, typically in binary form, according to instructions, which may be provided by a variable program. Exemplary computers, also called computing devices, include desktop computers, laptop computers, tablets, smartphones, and the like.

Examination region—an area located on an optical axis of a detection system at which an object, such as a sample (e.g., biological cells), can be examined optically (e.g., imaged with an image sensor).

Image—a representation of light detected at a two-dimensional or three-dimensional array of positions by an image sensor (e.g., a raw image), or a processed form thereof (e.g., a reconstructed image). A raw image may be an optically focused image or a hologram (i.e., a lensless image) created by lensless imaging, among others.

Image sensor—an optical sensor capable of detecting spatial variations (e.g., variations in intensity) of light in two dimensions, where the light is incident on a photosensitive detection area of the sensor. The image sensor may be a two-dimensional array sensor, such as a charge-coupled device (CCD) sensor, an active pixel sensor (e.g., a complementary metal-oxide-semiconductor (CMOS) sensor), a hybrid CCD-CMOS sensor, or the like. The image sensor may create a raster image (i.e., a bitmap) as a rectangular array of pixels, and may be configured to create color images, grayscale (monochromatic) images, or both.

Lensless imaging—capture of a diffraction pattern(s) for an object(s) (e.g., a sample including biological cells) using an image sensor. Lensless imaging is performed without interposing a lens between the object and the image sensor. The captured diffraction pattern (a hologram) can be called an image of the object(s) (e.g., an image of cells), even though the image is not an optically focused image. Since the image is not optically focused, the captured image generally is neither magnified nor minified relative to the object(s) (i.e., capture is with "unit magnification"). Accordingly, the photosensitive area of the image sensor should be at least as large as the floor of a well, if the entire floor is to be covered with the same lensless image. However, exemplary wells to be imaged may have a larger floor area than the photosensitive area of the image sensor. For example, the wells may be provided by six-well microplates or a single-well (e.g., rectangular) sample holder, among others. Accordingly, multiple lensless images for overlapping regions of the same well may be stitched together to generate a larger image representing more or all of the well's floor. Lensless imaging can include digital holographic reconstruction imaging, shadow imaging, or fluorescence imaging, or among others.

Lensless imaging may be performed with any suitable light source, which may epi-illuminate or trans-illuminate a sample, among others. The light source may illuminate the sample with coherent light (e.g., from a laser), partially coherent light (e.g., from a light-emitting diode), or incoherent light (e.g., with an incoherent light-emitting element and/or use of a diffuser in the illumination path). In some embodiments, the light source may trans-illuminate the sample with substantially plane wave illumination from an at least partially coherent light source. For example, the light source may be significantly farther than the image sensor from the sample along a z-axis, such as at least five or ten times farther. In some embodiments, the light source may include a light-emitting element optically coupled to a waveguide. The outlet of the waveguide may be mounted to an arm, which may be rotatable to change the sample illumination angle, and/or may be movable linearly to introduce sub-pixel shifts in the captured image.

Lensless images may be processed by pixel super-resolution techniques. Pixel super-resolution can produce sub-pixel resolution by laterally shifting the light source, the image sensor, and/or the sample, to create "sub-pixel" images, and then these sub-pixel images can be merged to obtain a smaller effective size of pixel.

Lensless images also or alternatively may be processed by phase-retrieval techniques. The captured raw image is an inline hologram containing intensity data. Lensless imaging can be used to reconstruct quantitative phase-contrast, which yields a representation for the volume of an object (e.g., cell) by means of pixel intensity. Moreover, lensless imaging can provide a large depth of field, so there may be no need for focusing. To retrieve the amplitude and phase of the sample, the phase-retrieval algorithm(s) used may require more than one hologram (due to the twin-image problem). Accordingly, the calculations for phase retrieval are advantageously performed with holographic image data from multiple holograms with similar fields of view (e.g., holograms captured with different sample-to-image sensor distances, different illumination angles, and/or different illumination wavelengths (e.g., using a tunable laser or light sources (e.g., laser diodes or LEDs) emitting at different wavelengths)).

Lensless imaging may be advantageous for the systems and methods of the present disclosure because bulky collection/detection optics are not required. Accordingly, microplates can be stored closer to one another in a vertical column of the microplates, because less space is needed for image capture under each microplate. The resulting incubation system is more compact and space-efficient.

Light—optical radiation, including ultraviolet radiation, visible radiation (i.e., visible light), and/or infrared radiation.

Light source—a device that generates light, optionally as a beam of light, and optionally powered by electricity. A light source includes at least one light-emitting element and also may include any associated optical element(s) to shape, size, filter, polarize, scatter, direct, and/or otherwise interact with light emitted by the light-emitting element(s). These optical elements may include any combination of at least one waveguide (e.g., a fiber optic or liquid light guide), lens, mirror, filter, diffuser, mask, aperture, beam-splitter, grating, prism, polarizer, and/or the like. Exemplary light-emitting elements include a semiconductor device, laser (e.g., excimer laser, gas laser, dye laser, solid-state laser, semiconductor crystal or diode laser, free electron laser, etc.), arc lamp, and/or the like. Exemplary semiconductor light-emitting elements include laser diodes, light-emitting diodes (LEDs), and superluminescent diodes, among others.

Microplate—a sample holder including a plurality of connected wells. The terms "microplate" and "plate" are interchangeable herein. The wells may be arranged in a planar, rectangular array, with the same uniform spacing along orthogonal horizontal axes, to form a plurality of rows and columns. The wells within a microplate may be substantially identical to one another, may be joined to one another, and/or may hold any suitable volume of fluid, such as between 1 microliter and 10 milliliters. The dimensions of the microplate may be according to American National Standards Institute (ANSI) and Society for Laboratory Automation and Screening (SLAS) (i.e., ANSI/SLAS) standards. For example, the microplate may have a 2 by 3 array of wells (such as 6, 12, 24, 48, 96, 384, or 1536 wells), a width of about 85 mm, a length of about 128 mm, a height of about 14 mm, and/or a well-to-well separation that is inversely related to the total number of wells. Exemplary well spacings include 3.6 cm, 1.8 cm, 9 mm, 4.5 mm, 2.25 mm, and 1.125 mm, among others. Each well may have a flat bottom to facilitate imaging. The microplate may be formed of a transparent polymer.

The microplate may include a lid to cover each well of the microplate. The lid is removable to permit dispensing to, and aspiration from, wells of the microplate.

Optics—a set of optical elements of an imaging system, which may be arranged along an optical axis between a light source and an examination region (illumination optics) and/or along an optical axis between the examination region and an optical sensor (collection optics). An optical element may be any device or structure that interacts with light, such as to collect, direct, focus, filter, polarize, scatter, collimate, and/or partially block light. An optical element may function by any suitable mechanism, such as reflection, refraction, scattering, diffraction, absorption, and/or filtering, among others. Exemplary optical elements include lenses, mirrors, diffusers, gratings, prisms, filters, apertures, masks, beam-splitters, waveguides, polarizers, and the like.

Optical sensor—a device that creates a signal (e.g., an electrical signal) in response to incident light. An optical sensor may be a point sensor or may have an array of light-sensitive elements to detect spatial differences in incident light. The array may be a one-dimensional array as in a linear sensor, a two-dimensional array as in an image sensor, or the like.

Robot—a device capable of moving and carrying out a series of actions under the control of a computer. Exemplary robots include a detection robot to detect light and/or capture images from plates, a plate robot to transport plates, a pipette robot to transfer liquid (e.g., into or out of wells of plates), a lid robot to remove and replace lids, and/or the like.

Sample—a specimen having any suitable properties. The sample may be organic and/or inorganic, natural and/or manufactured, and may include any suitable assembly, material, substance, isolate, extract, particles, or the like. In exemplary embodiments, the sample includes biological cells. The biological cells may be eukaryotic (e.g., mammalian cells) or prokaryotic (e.g., bacterial cells). Exemplary biological cells include established cells (cell lines), stem cells, primary cells, cells of a tissue sample, transfected cells, cells from a clinical sample (e.g., a blood sample, a fluid aspirate, a tissue section, etc.), clones of cells, or the like. A cell culture may include a set of cells, optionally contained by a well, and in contact with (e.g., immersed in) any suitable liquid medium. The liquid medium may be an aqueous medium, which may include water, salt, buffer, glucose, detergent, dye, protein, amino acids, or any combination thereof, among others. The liquid medium may be a growth medium for the cells.

Sample holder—a device for holding at least one sample or any array of spatially isolated samples, and optionally permitting the sample(s) to be imaged through a horizontal, transparent wall of the device (e.g., the bottom wall of a well). Exemplary sample holders are culture vessels including one or more wells, such as microplates, Petri dishes, cell culture flasks, etc.

II. Overview of Smart Incubators

This section provides an overview of automated incubation systems ("smart incubators") for processing samples held by sample holders, such as culturing and/or assaying biological cells held in wells of sample holders (as exemplified herein with microplates); see FIGS. 1-4.

FIG. 1 shows an exemplary smart incubator 50 in schematic form. Incubator 50 includes a housing 52 (e.g., a box) defining a main chamber 54, which may remain closed during operation of the incubator. The incubator also may have a storage structure 56 (interchangeably called a rack) for holding and organizing multiple sample holders, such as microplates 58, within main chamber 54, while cells contained by wells of the sample holders are being cultured.

Optical detection may be conducted in main chamber 54. Robotics may be used to move at least one optical sensor to every well of each microplate 58 (or other sample holder), for every microplate (or sample holder) stored in rack 56. More particularly, a detection robot 60 may optically sense contents of the sample holders, and particularly contents in each well thereof, while the sample holders remain in their respective storage sites within rack 56. For example, a detection robot 60 may capture images of cells growing in the wells. The detection robot may include a detection module having at least one light source 62 for illumination of a well and/or contents thereof, and at least one optical sensor, such as an image sensor 64, arranged to detect optical radiation from the illuminated well and/or contents, as described in more detail below. Detection robot 60 may be controllable to drive movement of the detection module thereof with at least three degrees of freedom (e.g., along three orthogonal axes), for optical alignment with each well of each microplate 58 (or other sample holder) of rack 56. More particularly, the detection robot and/or the detection module thereof, may travel horizontally, parallel to an array of storage locations defined by rack 56, indicated by arrows at 66, horizontally into and out of rack 56, orthogonal to the vertical array, indicated by a double-headed arrow at 68, and vertically. In some embodiments, detection robot 60 may have a separate, individually controllable motor (e.g., a servomotor) corresponding to each degree of translational freedom. Alternatively, or in addition, contents of microplates 58 or other sample holders may be optically sensed at a detection station 70 in main chamber 54 (or elsewhere in incubator 50), where the detection station is separate from rack 56. Detection station 70 may have a light source(s) and an optical sensor(s) as described herein for detection robot 60 but may be relatively fixed within main chamber 54 (or elsewhere in in incubator 50).

Detection robot 60 (and/or detection station 70) allows cell growth or development to be monitored. The detection robot may provide a compact, label-free imaging system for capturing one or more images of cells from every well of every microplate 58 (or other sample holder). The imaging system may be movable along three orthogonal axes, to reach every well of each microplate 58 supported by rack 56. This ensures that the optical axis (defined by the center of every microplate well to be imaged) is always vertical.

Detection robot 60 may include at least one light source 62 to be placed above and/or into each well of each microplate 58 (or other sample holder). Light source 62 may be a single light source having one light outlet optically coupled to a single upstream light-emitting element or a plurality of upstream light-emitting elements (e.g., of different color). The light source may have compact collimation optics and/or may utilize a diffuser near or at the light outlet. In some embodiments, light source 62 may be coupled or configured to be coupled to a special plate lid having a light guide reaching down into every well, deep enough to touch a liquid medium in the well, thereby avoiding an optical effect of the liquid meniscus. In some embodiments, light source 62 may transmit light from a light outlet having a small diameter (e.g., in the range of the size of a cell (such as a point source having a diameter of less than about 100, 50, 25, or 10 µm)), which provides a light source with high brilliance. For example, the light source may include a laser diode, mounted at a fixed place. A flexible fiber optic may be optically coupled to the laser diode and configured to act as a light guide for propagation of light from the laser diode, through the fiber, to a light outlet above a microplate well to be imaged. The light outlet may be movable in a horizontal plane with respect to the optical axis, to adjust the angle of illumination, which allows higher resolution from computer-aided image reconstruction. In some embodiments, the light source may include an array of compact point light sources each having a small diameter (e.g., less than about 100, 50, 25, or 10 µm), for example, an organic LED display as a matrix of small light sources that can be controlled individually. This configuration permits single point illumination or a pattern of illumination by a combination of light sources of the matrix, which may provide higher resolution from computer-aided image reconstruction as well as enable illumination enhancement strategies for compensating negative effects of the liquid meniscus Detection robot 60 also may include at least one image sensor 64 to be placed under each microplate (or other sample holder). Each image sensor 64 may be configured to capture an image of the entire floor of a microplate well (and the cells thereon). Alternatively, the entire floor (and cells thereon) may be imaged by capturing a plurality of tiled images. The image sensor may be provided by a compact camera with integrated, compact optics (e.g., a small CMOS camera with compact optics). In other embodiments, the image sensor may be exposed directly to the illumination rays from one or multiple point sources above the microplate, without any intervening optics between the bottom of microplate 58 and the image sensor 64 to focus light rays. In some embodiments, image sensor 64 may be lenslessly exposed to the illumination rays from a source of diffuse light located above the microplate, if only low optical resolution is needed. However, imaging may be performed with any type of imaging in any of the incubation systems disclosed herein.

A fluid handling station 72 in main chamber 54 may perform transfer of fluid into and out of wells of microplates 58 and/or other plates. The fluid handling station may have a plate dock 74 with one or more plate receiving sites (interchangeably called docking sites) to hold one or more microplates and/or other plates at predefined positions. Plate dock 74 may be fixed or movable. The plate dock may provide a position for a master plate, typically with deep wells, which may be loaded into the incubator via a dedicated door, or via one of the other doors described elsewhere herein. A lid robot 76 may be configured to remove lids from plates located in plate dock 74, to permit fluid addition to, and/or removal from, wells of the plates with at least one pipette 78, and to replace the lids when fluid transfer is complete. Each pipette 78 may include a pump 80 to drive fluid into and/or out of an end of the pipette, a motor-driven positioner to move the end of the pipette precisely in three dimensions, and/or a tip ejector to remove pipette tips 82 from the end of pipette 78 after use. The pipette(s) may be able to operatively access each well of each plate located in plate dock 74, for fluid addition and/or removal. Pipette tips 82 may be stored in at least one of two different stack positions (e.g., to create respective stacks of tip boxes) in the fluid handling station. At least one of the stack positions may be employed for storing new pipette tips that have not yet been used by the pipette. At least one other of the stack positions may be employed for storing pipette tips that have already been used by the pipette. Any suitable culture media and reagents 84 may be accessible to pipette 78 of fluid handling station 72 for uptake and/or dispensing. The media and reagents may be contained in vessels (e.g., bottles), which may be stored inside or outside chamber 54 and/or housing 52. Exemplary reagents include buffered saline, trypsin, assay solutions, test compounds, and the like. At least one stack of assay plates 86 (and/or transfer plates) may be stored in fluid handling station 72 and transferred individually (e.g., by a plate robot), as needed, to one of the plate receiving sites of plate dock 74 when assay mixtures are to be created in wells of assay plates 86.

Assay plates 86 may be used to test the supernatant of cell cultures contained in wells of microplates 58, for the presence/level of a given analyte and/or activity (e.g., a binding activity of a monoclonal antibody). Each microplate 58 may be moved to plate dock 74 and a sample of the supernatant contained in one or more of the wells may be transferred to one or more wells of an assay plate 86. Each assay plate may be an ELISA plate having wells coated with a reagent (e.g., an antibody, an epitope, or the like). In other examples, each assay plate 86 may be an uncoated plate that will be moved out of the incubator to an external liquid handler. In yet other examples, each assay plate 86 may receive supernatant from a well and reagents to support a homogeneous test, which may be performed inside or outside the incubator.

Test compounds and/or liquid for feeding cells may be added to and/or removed from wells of microplates 58 at fluid handling station 72, or in a separate, dedicated station inside the incubator, or while microplates 58 remain in rack 56. Accordingly, compound addition and/or feeding cells (e.g., changing media by removal of old media and addition of new media) may be performed using a reagent dispenser (fluid addition only), a low-volume pipettor (fluid addition and removal), or microfluidics plates (fluid addition and removal). The microfluidics plates may be hydraulically connected at each storage position of rack 56, at fluid handling station 72, or in a separate dedicated station. Single cell dispensing may be performed in the incubator by or near fluid handling station 72.

A plate robot 88 may transport microplates 58 within main chamber 54, and optionally out of the main chamber. The plate robot may transport microplates 58 to and from individual storage positions within rack 56. More generally, plate robot 88 may move microplates 58 within, between, or among rack 56, detection station 70, and/or fluid handling station 72. The plate robot also may move boxes of pipette tips 82 and/or assay plates 86 within fluid handling station 72 and/or chamber 54. Plate robot 88 may be controllable to drive movement of a plate-grasping structure 90 thereof with three degrees of translational freedom (e.g., along three orthogonal axes). For example, plate-grasping structure 90 may travel horizontally along rack 56, indicated by arrows at 92, horizontally into and out of rack 56, indicated by a double-headed arrow at 94, and vertically. In some embodiments, the plate robot may have a separate, individually controllable motor (e.g., a servomotor) corresponding to each degree of freedom.

A computer 96, such as a local computing device, controls and automates operation of incubator 50 using a processor 98. The computer may be connected, in a wired or wireless fashion, indicated at 100, to each of the stations, robots, systems, and electrical devices of incubator 50. These connections may permit the computer to receive signals from and/or send signals to any suitable combination of stations, robots, systems, and/or devices of the incubator. Accordingly, the computer coordinates operation of incubator 50, and may interface with a local user directly. Computer 96 also or alternatively may interface with a user via a communications network, such as a wide area (telecommunications/computer) network (WAN) 102 (e.g., the Internet), and a remote computing device 104 operated by the user.

Computer 96 may have any suitable hardware to facilitate communication with, and/or operation of, processor 98. Exemplary hardware includes memory 106 storing instructions for processor 98 to perform and/or control any suitable procedures, as described herein. Exemplary user interfaces that may be suitable include an input device 108 (e.g., a keyboard, keypad, mouse, touchscreen, etc.) and an output device 110 (e.g., a monitor, printer, touchscreen, etc.). In some embodiments (e.g., with a touchscreen), the same device may handle input from the user and output from the processor.

Incubator 50 may include any suitable sensors and may perform automated plate and fluid handling and imaging of cells. The sensors and automation may include, but are not limited to, one or more image sensors, pH sensors, $O_2$ sensors, robotic arms, fluid level sensors, cell media health sensors, temperature sensors, $CO_2$ sensors, automated cell culture media replenishment, and pressure sensors. All of these sensors are remotely operable by a user, and results from any of the sensors may be monitored anywhere, anytime by a user over the Internet via a remote computing device 104, which may be a mobile device.

Computer 96 may obtain all measurement data and be able to control and coordinate the workflow of cultivating/assaying cells. Input data may be collected by computer 96. Exemplary input data includes any combination of the following: (1) captured images of single or multiple cells in every microplate well, (2) cell count or cell density/confluence data for each well from captured images, (3) pH and/or oxygen data for every well (e.g., if needed for a specific cell culture cycle), (4) colorimetric information from an indicator in the cell culture medium, (5) loading data for transfer of single cells or cells from a bulk solution to microplates 58 (optional if run starts with monoclonal cells), and/or (6) potential contamination data for the incubator, among others.

The computer may perform various actions automatically, as needed, based on input data. For example, the computer may decide whether, when, and/or how to perform any of the following: (1) feeding cells in each well when appropriate, (2) correcting pH and/or oxygen levels in wells by adding appropriate reagents, (3) removing excess media from wells, (4) transferring media/cells from wells of microplates 58 to wells of assay plates, such as when a defined confluency is reached, (5) reporting when microplates 58 are ready to be used at a defined level of confluency in at least one well of microplate 58, (6) passaging cells (e.g., using trypsin or similar reagents) into one or more new sample holders to restart the incubation process, (7) transferring cells into containers for storing or freezing cells outside the system, and/or (8) adding reagents or compounds once a defined confluency is reached, among others.

Computer 96 may create output data from input data. Exemplary output data includes any combination of (1) the growth rate of cells in each well of each microplate, (2) identification of wells not containing living cells, (3) identification of contaminated wells, (4) the level of each reagent available, and (5) the response, if any, of each cell culture in each well to addition of a test compound(s) and/or reagent (s).

Main chamber 54 may have a climate that is controlled by a climate control system 112. Exemplary climate parameters of main chamber 54 that may be monitored and/or regulated by climate control system 112 include temperature, gas levels (e.g., $CO_2$, oxygen, etc.), humidity, particulate levels (e.g., by filtering), airborne and/or surface microorganism levels (e.g., by ultraviolet radiation), any combination thereof, or the like. The climate control system may include a thermal control system 114, which may be composed of one or more heaters to heat (and maintain) main chamber 54 above the ambient temperature at a temperature set point, one or more temperature sensors, a set point controller, one or more fans to circulate gas inside the chamber, or the like. The climate control system also may include a source of water for humidification, one or more humidity sensors, a source of carbon dioxide (such as a $CO_2$ tank), a $CO_2$ sensor(s), one or more air/gas filters, at least one ultraviolet light source to kill microorganisms within the main chamber before/during use of the incubator, or any combination thereof, among others.

Figure 2:
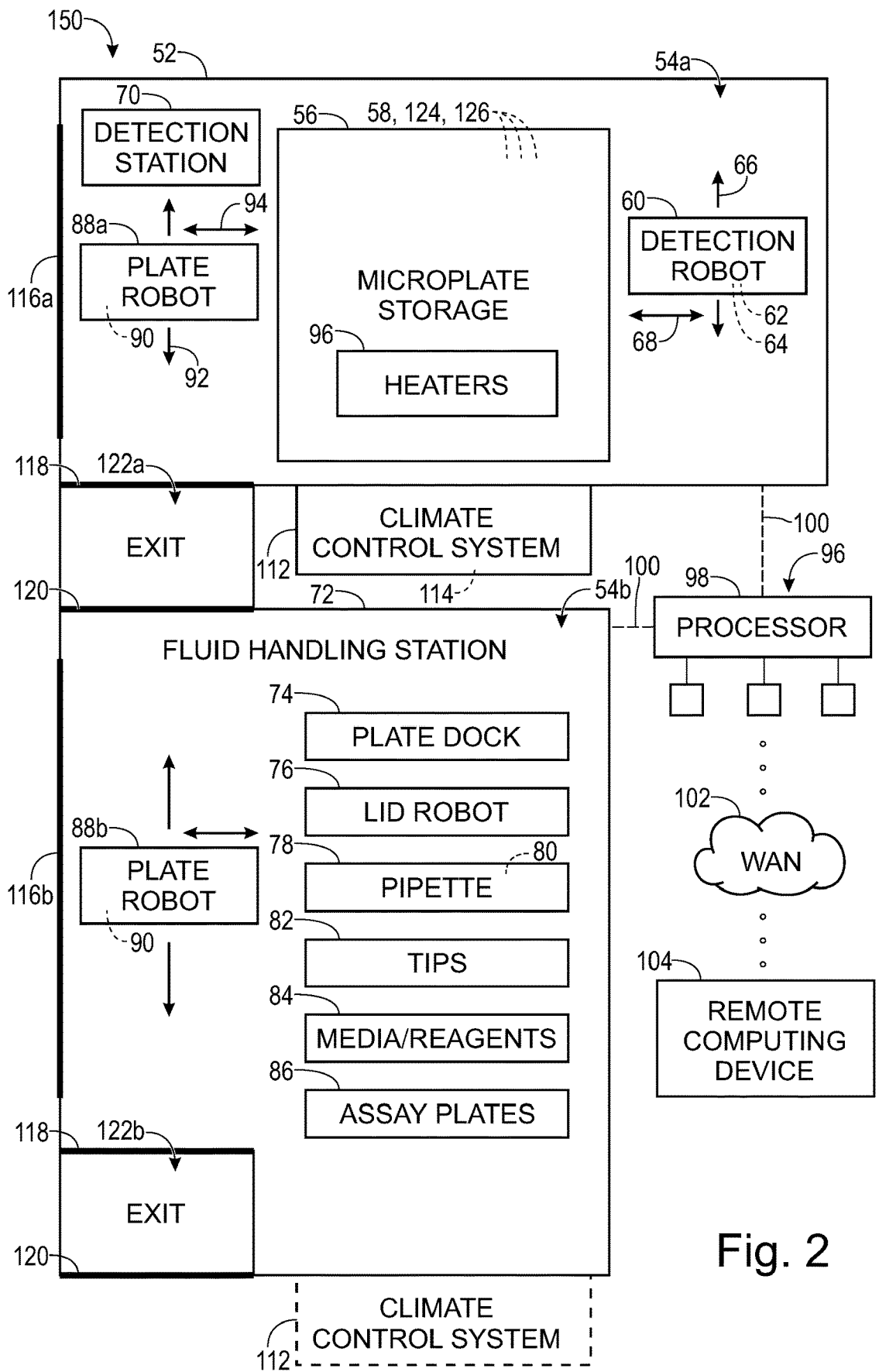
FIG. 2 is a schematic top view of another exemplary smart incubator for culturing and/or testing biological cells, wherein the smart incubator has separate but connected chambers for storage of sample holders and handling of fluid, in accordance with aspects of the present disclosure.

Main chamber 54 can be accessed via one or more doors, which are represented in FIGS. 1 and 2 by heavier lines. A larger maintenance door 116 may provide access to all areas inside the incubator, to allow introduction/removal of consumables (e.g., plates, tips, reagents, etc.), cleaning, disinfection, servicing, or the like. Accordingly, maintenance door 116 may be opened while the incubator is being readied for use, and then may remain closed while cells are being cultured/assayed. A pair of smaller doors, namely, an inner door 118 and an outer door 120, may permit items (e.g., plates) to be passed into and out of main chamber 54 via an entry/exit chamber 122 (interchangeably called an interface chamber), while incubator 50 is operating, and without opening chamber 54 directly to the external environment. The entry/exit chamber may, for example, be sized to hold only one plate or a stack of two or more plates, among others. The entry/exit chamber may include a rack to organize and/or vertically separate plates. Entry/exit chamber 122 communicates with main chamber 54 via inner door 118 and with the external environment via outer door 120. Doors 118, 120 may be opened and closed sequentially to allow entry/exit chamber 122 to be loaded and then emptied. For example, inner door 118 may be opened and closed first, to allow automated loading of entry/exit chamber 122 from main chamber 54 (e.g., using plate robot 88), and then outer door 120 may be opened to allow manual or automated unloading of entry/exit chamber 122 from outside incubator 50. Alternatively, outer door 120 may be opened and closed first, to allow manual or automated loading of entry/exit chamber 122 from outside incubator 50, and then inner door 118 may be opened, to allow automated unloading of items (e.g., using plate robot 88), from entry/exit chamber 122 into main chamber 54, and then closed. Opening and closing of inner door 118 or each door 118, 120 may be controlled automatically, and optionally driven by a motor.

Rack 56 has a plurality of storage positions 124 to support microplates 58 or other sample holders. Storage positions 124 may be arranged in an array, generally at least a two-dimensional or a three-dimensional array of such positions 124. For example, at least a subset of the storage positions may be arranged in a plurality of vertical columns and a plurality of horizontal rows, with each column and row having at least two, three, or more storage positions 124. In some embodiments, rack 56 may be open on opposite sides, such that each storage position 124 and/or a microplate 58 supported by rack 56 at the storage position, can be operatively accessed from the opposite sides by detection robot 60 and plate robot 88, optionally at the same time as one another. For example, in FIG. 1, detection robot 60 and plate robot 88 access each storage position 124 from the right and left sides, respectively, of rack 56, as described further below. Accordingly, detection robot 60 and plate robot 88 may have ranges of motion that do not substantially overlap, so that both robots can perform their respective functions at the same time without interfering with one another.

A plurality of local heaters 126 may be incorporated into rack 56 to enable lids of microplates 58 (or other sample holders) to be heated before image capture, to reduce condensation on the inside surface of each lid. Water droplets on the inside surface can scatter incident optical radiation received from a trans-illumination light source positioned above the lid. This scattering may degrade the quality of images captured from the cells contained in microplate wells. Each storage position 124 may include a dedicated heater 126, which may be located in the upper portion of the storage position, above the corresponding stored microplate 58. For example, the heater may be arranged vertically above the lid of a microplate supported in the storage position, close enough to heat the microplate lid when the heater is energized, but spaced sufficiently to permit detection robot 60 to operatively access each well of the microplate (also see below). Heaters 126 are controllable with computer 96, optionally individually (i.e., independently) for each storage position 124. Each heater 126 associated with a storage position 124 may be energized suitably in advance of imaging cells located in the storage position, to allow sufficient heating time for condensation to be eliminated. For example, the heater may be turned on about 10, 20, or 30 minutes or one hour before imaging is performed. Exemplary heaters that may be suitable include resistive heaters (e.g., sheet heaters), thermoelectric heaters, optical heaters, or the like. Each heater may underlie a layer of insulation, to minimize undesired heat transfer to a microplate located above the storage position 124 to be heated.

FIG. 2 shows another exemplary smart incubator 150 in schematic form. Incubator 150 may have any of the components described above for incubator 50, as indicated by the same reference numbers as in FIG. 1. However, incubator 150 differs from incubator 50 by separating microplate storage in rack 56, and fluid transfer with fluid handling station 72, to a culture chamber 54a and a fluid handling chamber 54b inside different portions of housing 52. Culture chamber 54a may be climate-controlled by a dedicated climate control system 112, while fluid handling chamber 54b may or may not be climate controlled by the same or a different climate control system 112, as indicated by a dashed rectangle. Movement of microplates 58 and other plates inside chambers 54a, 54b may be performed by respective plate robots 88a, 88b, each capable of grasping microplates and other plates and moving them in three dimensions.

Each chamber 54a, 54b may be accessed through one or more doors. A large maintenance door 116a or 116b may provide access to respective chambers 54a, 54b, as described above for maintenance door 116 of incubator 50. Chambers 54a, 54b may be connected to one another via at least one door, which may be controlled by computer 96. In the depicted embodiment, chambers 54a, 54b are connected by an inner door 118 and an outer door 120, each of which opens to an entry/exit chamber 122a. Doors 118, 120 may operate as described above for incubator 50. Fluid handling chamber 54b may be accessed from outside incubator 150 via an inner door 118 and an outer door 120, each of which opens to an entry/exit chamber 122b, as described above for incubator 50. A microplate 58 may be removed from chamber 54a during operation of the incubator using plate robot 88a to transport the microplate to entry/exit chamber 122a, and then plate robot 88b to transport the microplate to entry/exit chamber 122b. Alternatively, the microplate may be removed from incubator via entry/exit chamber 122a and maintenance door 116b if climate control and/or contamination in fluid handling chamber 54b is of less concern.

In some embodiments, detection station 70 may be located in fluid handling chamber 54b. Assay plates prepared in fluid handling chamber 54b also may be incubated in the chamber, optionally at an elevated temperature, and then transported within chamber 54b to detection station 70 for reading results of assays.

Figure 3:
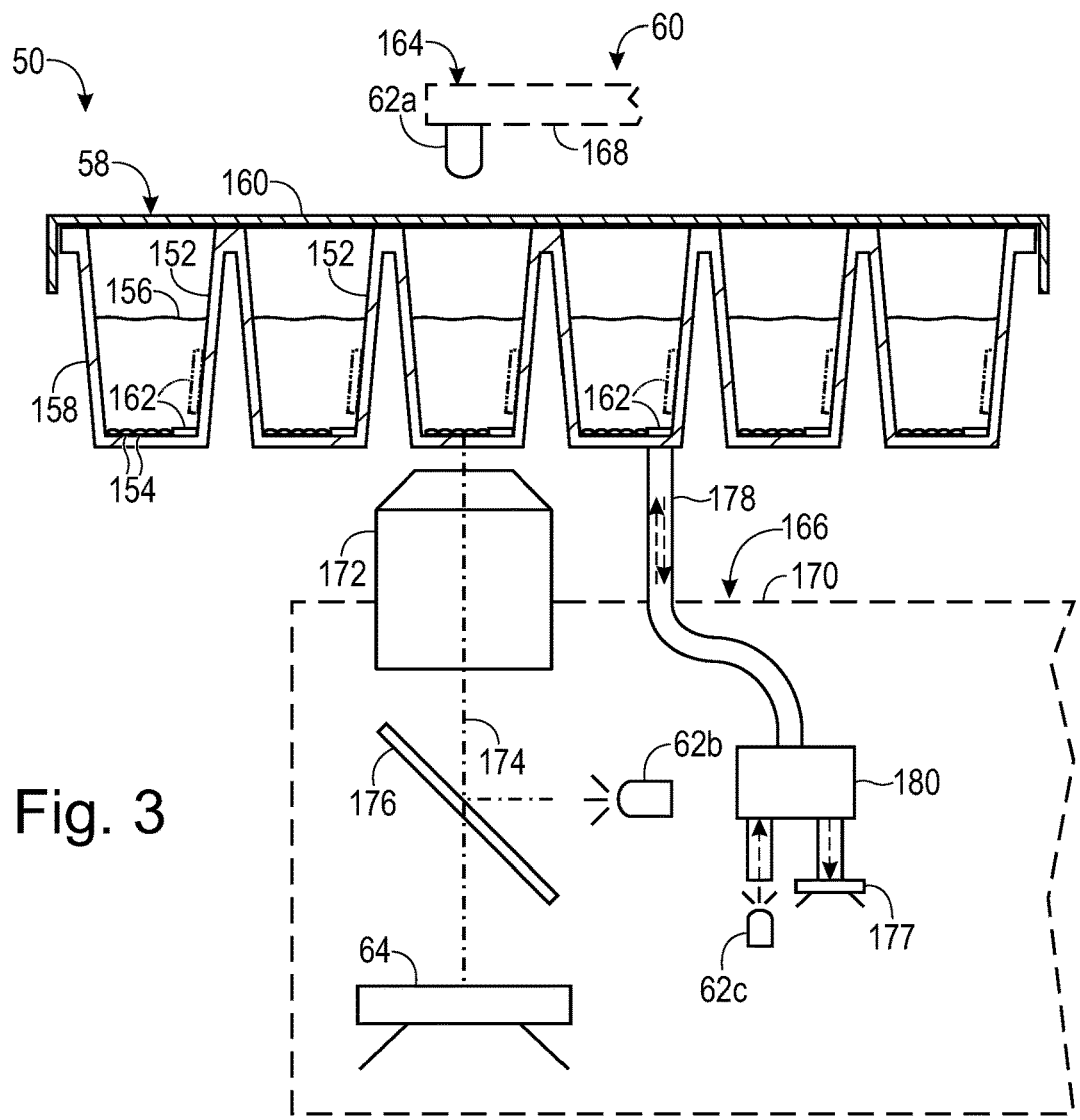
FIG. 3 is a partially sectional, somewhat schematic view of a microplate containing cell cultures and operatively arranged with respect to a detection module of a detection robot of the smart incubator of FIG. 1 or 2, in accordance with aspects of the present disclosure.

FIG. 3 shows an exemplary microplate 58 having a plurality of wells 152 each containing a culture of biological cells 154 disposed in a liquid growth medium 156. Wells 152 are formed by a transparent body 158 and covered by a transparent lid 160. Cells may be located on the floor of the well, optionally adhered thereto, and arranged in a monolayer.

Incubator 50 also may have an additional detection assembly to monitor the pH, oxygen, and/or carbon dioxide level of growth media inside each well 152 of each microplate 58. The detection assembly may be provided by detection robot 60 or by detection station 70, among others. Each microplate well 152 may contain at least one chemical sensor 162 (e.g., at least one sensor spot) to sense pH, oxygen, and/or carbon dioxide levels as photoluminescence (e.g., fluorescence) from the sensor(s). Each chemical sensor 162 may be mounted on the floor of the well (shown in solid outline), if single cell detection is not required, or on a side wall of the well (shown in phantom outline) to allow imaging of the entire well bottom. Chemical sensors 162 may be placed into wells 152 when they are empty, before cells 154 are added in liquid growth medium 156. In other embodiments, chemical sensors 162 may be mounted on additional rods reaching into medium 156 from microplate lid 160. Each chemical sensor 162 may be configured to sense pH, oxygen, or carbon dioxide, among others, when excited with suitable optical radiation. Excitation may induce a detectable photoluminescence characteristic that corresponds to the pH, oxygen concentration, or carbon dioxide concentration in medium 156. Exemplary commercially-available chemical sensors that may be suitable are self-adhesive pH, oxygen, or $CO_2$ sensor spots from PreSens Precision Sensing GmbH.

FIG. 3 shows an exemplary detection module 164 for detection robot 60 (or detection station 70). Detection module 164 is operatively aligned with a pair of wells 152 of microplate 58 for imaging of one well and optical detection of photoluminescence from chemical sensor 162 in an adjacent well 152. The detection module may include a housing 166 (interchangeably termed a frame) having an upper arm 168 and a lower arm 170, which may be firmly attached to one another or actively movable relative to one another (e.g., along a vertical axis).

Arms 168, 170 are shown as dashed and fragmentary here to focus attention on the optical components supported by the arms. At least one trans-illumination light source 62a may be mounted to upper arm 168 for illuminating each well 152 from above the microplate, as described elsewhere herein. Lower arm 170 may support an objective 172 and an image sensor 64. The objective may collect and optionally focus optical radiation from light source 62a that has propagated downward through the well. Image sensor 64 captures images of cells 154 by detecting the optical radiation.

Detection module 164 also may be configured to detect photoluminescence from cells 154, and, optionally, chemical sensor 162. An epi-illumination light source 62b may be supported by lower arm 170. Light source 62b is shown generating optical radiation for excitation of photoluminescence from cells 154 in FIG. 3. The optical radiation may propagate along an optical axis 174 to a beam-splitter 176, which reflects the optical radiation upward, for propagation through objective 172 to cells 154. Photoluminescence from cells 154 can be collected by objective 172 for propagation downward through beam-splitter 176 to image sensor 64.

An optical property of chemical sensor 162 may be detected using any suitable illumination source and optical sensor. Photoluminescence from chemical sensor 162 may be induced by excitation with any suitable light source, such as trans-illumination source 62a, epi-illumination source 62b, or a different epi-illumination source 62c, among others. Photoluminescence may be detected with image sensor 64 (e.g., in a captured image representing cells and chemical sensor 162, or chemical sensor 162 alone). Alternatively, or in addition, an optical property of chemical sensor 162 may be detected using a separate optical sensor 177 (e.g., a point sensor), which may be optically coupled to a waveguide 178, along with source 62c, via a coupler 180. This arrangement allows excitation light and emitted light to propagate in opposite directions along waveguide 178. In the depicted embodiment, waveguide 178 and image sensor 64 are aligned with chemical sensor 162 and cells 154 in adjacent wells. In other embodiments, waveguide 178 and image sensor 64 may be closer to one another, such that they can be concurrently aligned with chemical sensor 162 and cells 154 in the same well 152. Light from chemical sensor 162 that has propagated downward through the bottom wall of well 152 may be detected, as shown here. Alternatively, light may be detected that has passed laterally from well 152 through a side wall thereof, if chemical sensor 162 is located on the side wall (as shown in phantom in FIG. 3). In that case, waveguide 178 may be oriented and positioned suitably (e.g., obliquely) for efficient optical coupling with the chemical sensor according to its side wall location.

Figure 4:
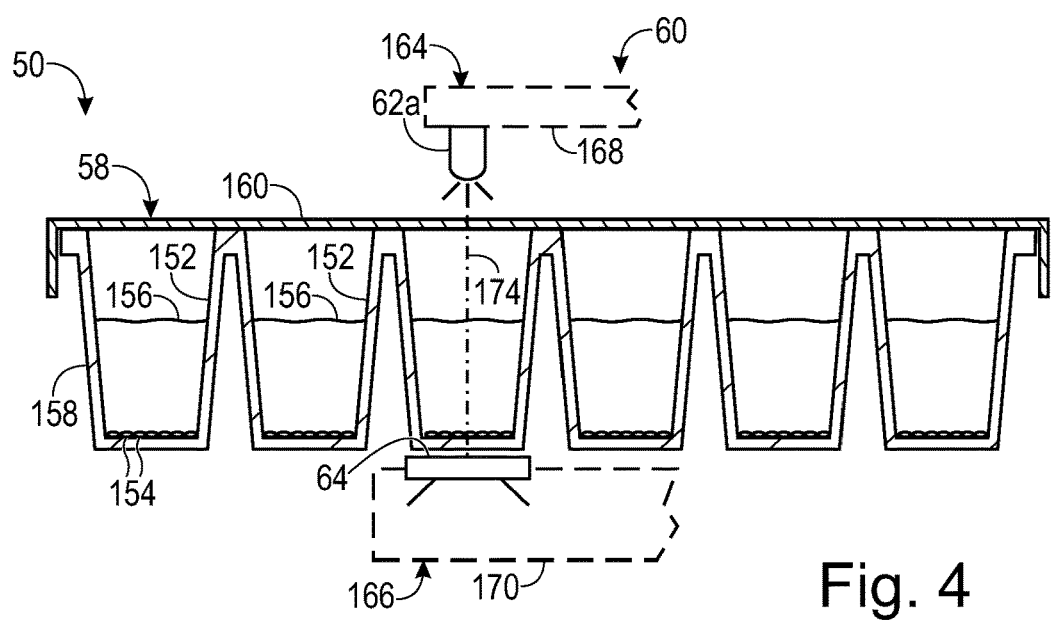
FIG. 4 is a partially sectional, somewhat schematic view of a microplate containing cell cultures and operatively arranged with respect to a lensless imaging module of the detection robot of FIG. 1 or 2, in accordance with aspects of the present disclosure.

FIG. 4 shows an exemplary lensless imaging configuration for detection module 164 of detection robot 60. The floor of well 152 and cells 154 thereon may be illuminated at only one angle, or successively at different angles to facilitate capture of an image at each angle. Light source 62a may include an array of light-generating elements that can be selectively energized to change the illumination angle or pattern, or an outlet of light source 62a may be movable to change the illumination angle. Image sensor 64 may be supported by lower arm 170 under and adjacent a well 152 of microplate 58. Cells 154 in well 152 may be imaged lenslessly by image sensor 64, that is, without an intervening lens to gather/focus light below the cells (e.g., without objective 172 of FIG. 3). It may be necessary or desirable to remove the lid with plate robot 88 before capture of lensless images. Further aspects of lensless imaging that may be suitable are described above in Section I.

III. Methods of Sample Incubation and Processing

This section describes exemplary methods of sample incubation and processing performed with the smart incubators disclosed herein, as exemplified with incubator 50 (see FIGS. 1-4). The method steps described in this section may be performed in any suitable order and combination, using any of the smart incubator configurations and features of the present disclosure.

Incubator 50 may be cleaned and decontaminated before the start of a cell culture cycle. System liquids (e.g., liquids for fluid handing station 72) may be filled. Materials, such as pipette tips 82 in boxes and assay plates 86, may be loaded into main chamber 54 of the incubator via maintenance door 116. Microplates 58 having lids 160 may be loaded into incubator 50. In some cases, microplates 58 containing cells in liquid growth medium may be prepared outside incubator 50 and then loaded directly into the appropriate storage positions 124 of rack 56. Alternatively, empty microplates 58, including lids 160, may be placed into incubator 50, such as in appropriate storage positions 124 of rack 56. The incubator then may automatically load single cells or multiple cells into individual wells 152 of microplate 58 along with the appropriate volume of growth medium. In some embodiments, the cells may be loaded from bulk solution or from wells of a master plate. Microplates 58 may be equipped with chemical sensor devices 162 for measuring pH and oxygen concentration in every well 152. An appropriate cell culture protocol may be inputted to control computer 96, and then the run may be started after initial priming of chamber 54 with gas and humidity.

Images may be captured of cells contained in wells 152 of microplates 58 (or other sample holders). The images for each microplate may be captured by an image sensor 64 of a detection robot 60, while the microplate remains in its storage position 124 in a rack 56 inside incubator 50. In other words, detection robot 60 may move image sensor 64 into vertical alignment with each well 152 of a microplate while the microplate is supported by rack 56, and then one or more images of cells in the well may be captured. Each image may cover the entire floor of the well, or only a portion thereof (e.g., less than one-half the floor's area).

Before image capture for a given microplate 58, lid 160 of the microplate (or other sample holder) may be heated with a heater 126 located above the lid in rack 56. Heater 126 may be a dedicated heater for only one microplate storage position 124 within rack 56, and/or may be controllable independently of heaters 126 for other microplate storage positions 124. Accordingly, heating may be performed locally within the incubator, and for only a short time, to minimize temperature fluctuations in chamber 54.

Microplates 58 (or other sample holders) may be moved from rack 56 to fluid handling station 72 inside the incubator using a plate robot 88. Each microplate may be moved in anticipation of fluid transfer to/from one or more wells 152 of the microplate. Accordingly, the microplate may be moved if one or more captured images of cells contained by the microplate meet one or more predefined criteria indicating that fluid transfer is needed or appropriate. The predefined criteria may relate to cell number/confluence/density, morphology, size, or other measurable parameters of cells in one or more wells of the microplate. For example, the microplate may be moved to fluid handling station 72 for feeding splitting, exposure to a test compound, and/or assaying (using a removed volume of the culture supernatant), if one or more wells of the microplate have at least a threshold number/confluence/density of cells. In some embodiments, a user may view captured images, optionally via the Internet, and decide whether/when computer 96 should move a given microplate to fluid handling station 72 for fluid addition/removal.

Liquid may be transferred into and/or out of at least one well of the microplate (or other sample holder) at fluid handling station 72. The fluid transferred may include liquid growth (culture) medium. For example, an old volume of culture medium in the at least one well may be replaced with a new volume of culture medium. In other cases, the fluid transferred may contain a test compound. For example, the test compound may be added to the at least one well in a volume of carrier liquid, without changing the culture medium. In yet other cases, the fluid transferred may contain a volume of supernatant and/or cells from the at least one well, and may be transferred to a well of another plate. Supernatant may be transferred for testing in any suitable type of assay. Cells may be transferred for testing and/or subculturing.

IV. EXAMPLES

This section describes selected aspects and embodiments of the present disclosure related to smart incubators and methods performed with smart incubators. Any suitable aspects of incubators and methods described in this section may be combined with one another and/or with any suitable aspects of the incubators and methods disclosed elsewhere in the present disclosure. These examples are intended for illustration only and should not limit or define the entire scope of the present disclosure.

Example 1

Smart Incubator Embodiment

This example describes selected aspects of an embodiment 250 of smart incubator 50 of Section II; see FIGS. 5-8.

Figure 5:
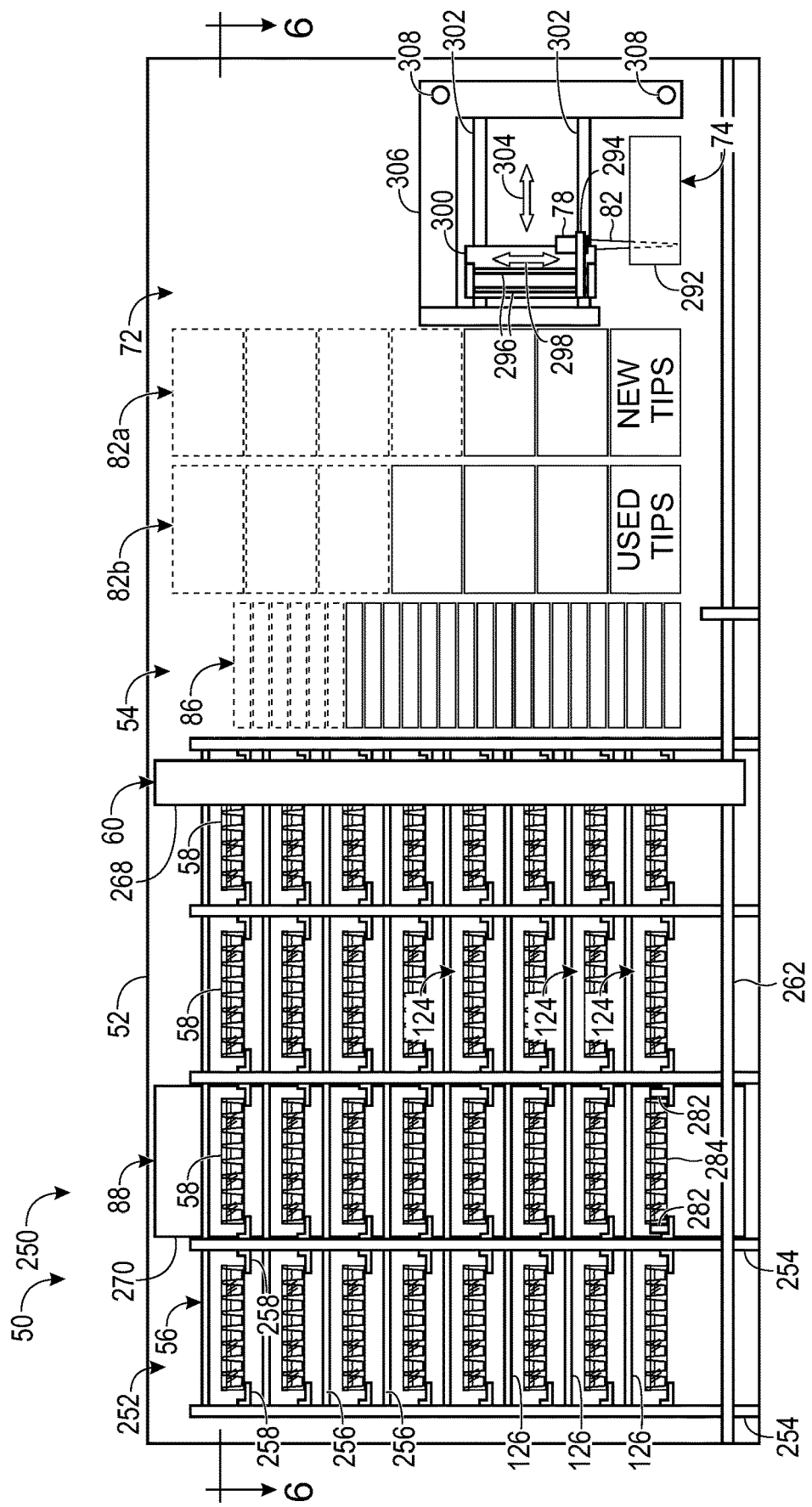
FIG. 5 is an elevational view of selected aspects of an exemplary embodiment of the smart incubator of FIG. 1, taken with the incubator operatively loaded with microplates and other consumables, and with a side wall of the incubator's housing removed to reveal internal components, in accordance with aspects of the present disclosure.
Figure 6:
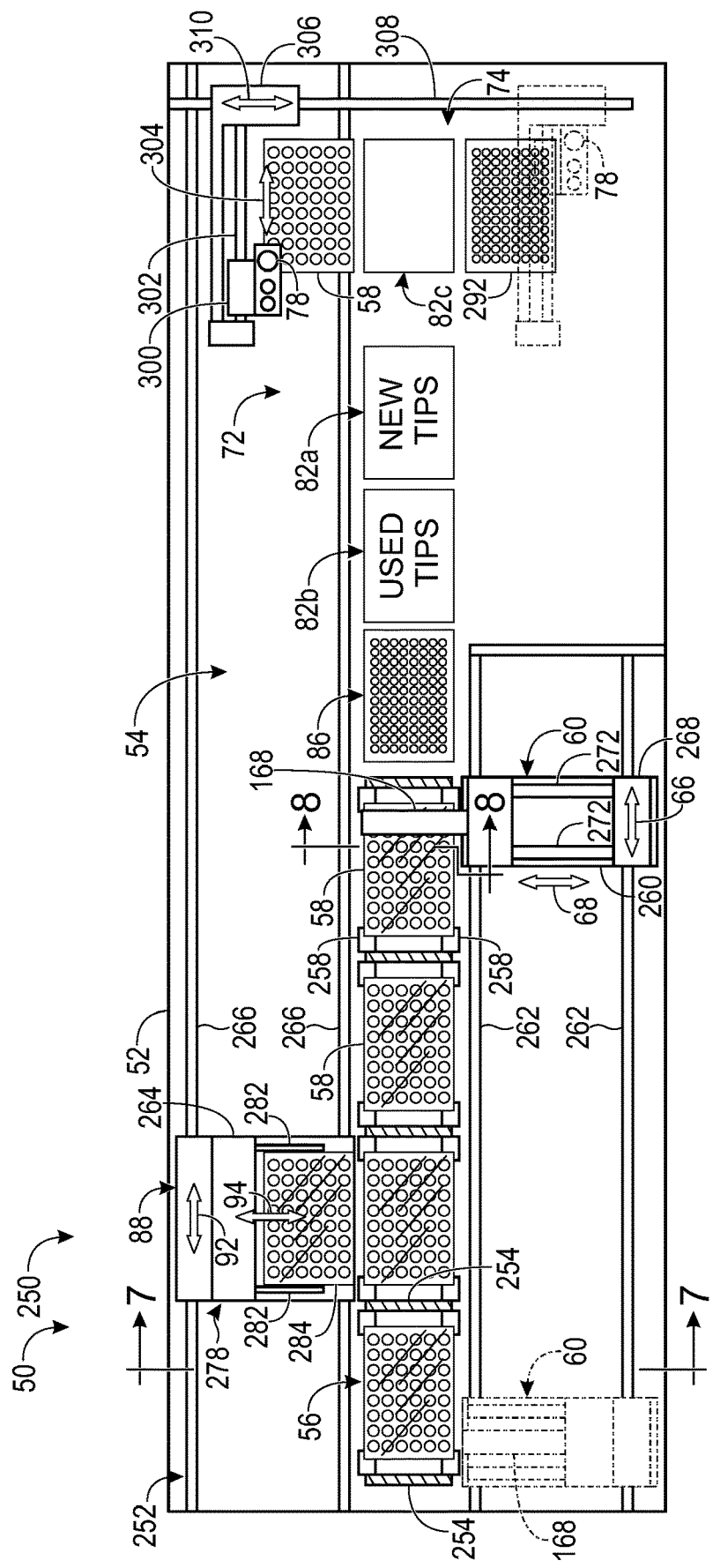
FIG. 6 is a sectional top view of the operatively-loaded incubator of FIG. 5, taken generally along line 6-6 of FIG. 5.
Figure 7:
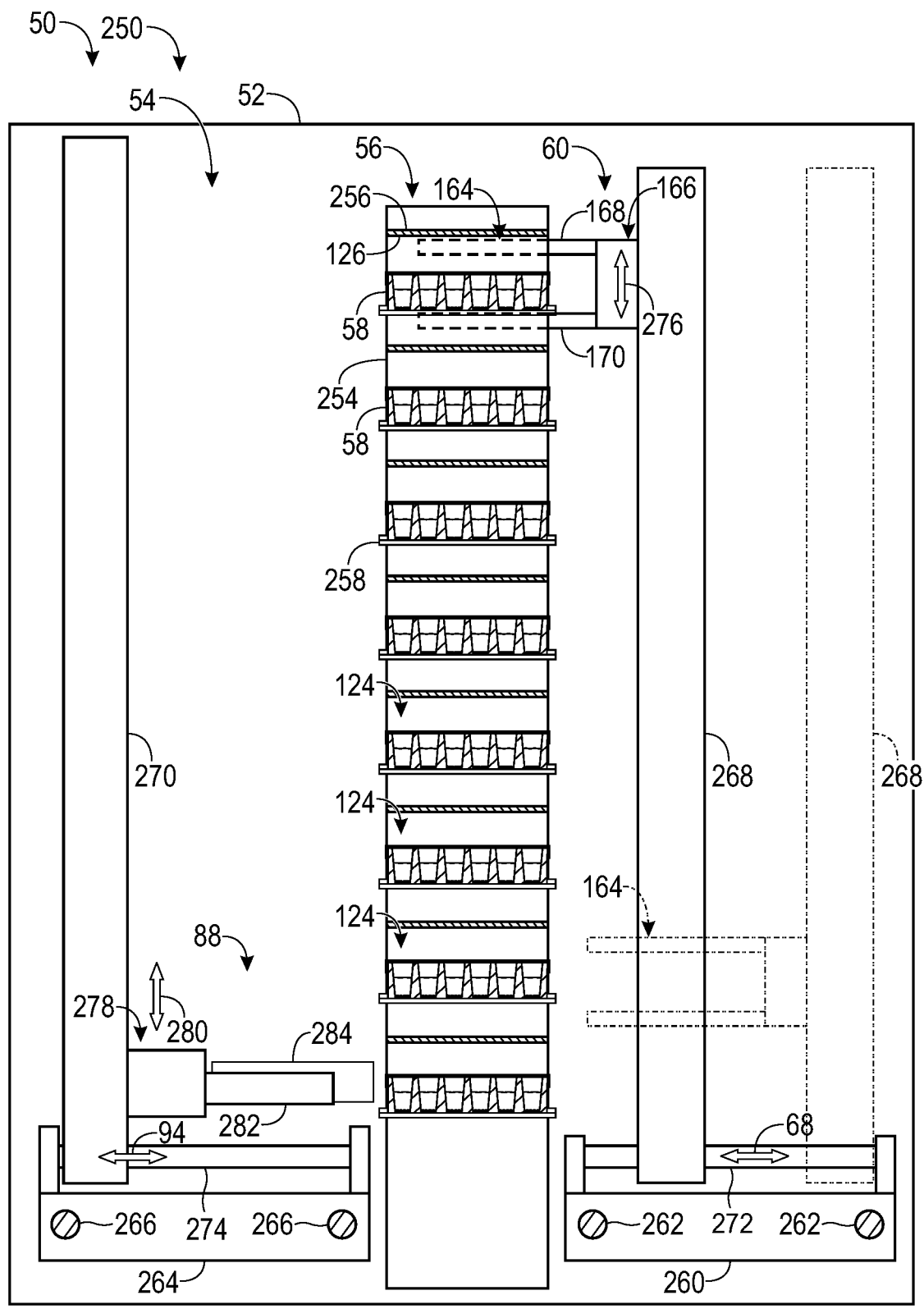
FIG. 7 is a sectional view of the operatively-loaded incubator of FIG. 5, taken generally along line 7-7 of FIG. 6.

FIGS. 5, 6, and 7 respectively show a side view, a sectional top view, and a sectional end view of incubator 250. The incubator is generally divided into a storage station 252, on the left in FIGS. 5 and 6, and a fluid handling station 72 on the right.

Storage station 252 includes a rack 56 holding a plurality of microplates 58 arranged in horizontal rows and vertical columns. The rack has a frame composed of vertical wall members 254 mounted on a floor of housing 52. Horizontal wall members 256 attach adjacent vertical wall members 254 to one another above the floor. A respective heater 126 is located on a bottom side of each horizontal wall member 256. Brackets 258 are mounted to vertical wall members 254 to create a storage position 124 for supporting a microplate 58 under each heater 126. Suitable clearance around microplate 58 in storage position 124 for access by a detection robot 60 (above and below the microplate) and a plate robot 88 (below and/or adjacent opposite lateral sides of the microplate) is created by the relative vertical positions of horizontal wall members 256 and brackets 258.

Detection robot 60 and plate robot 88 also are operative in storage station 252. Robots 60, 88 are configured to access microplates 58 from respective opposite sides of rack 56. Detection robot 60 has a carriage 260 that can be driven horizontally, indicated at 66, along the front side of rack 56, on front rails 262 (see FIGS. 6 and 7). Similarly, plate robot 88 has a carriage 264 that can be driven horizontally, indicated at 92, along the back side of rack 56, on back rails 266. Back rails 266 are longer than front rails 262, to permit plate robot 88 to travel outside storage station 252 in chamber 54. This larger range of travel allows plate robot 88 to move plates (such as microplates 58) between rack 56 and fluid handling station 72, within the fluid handling station, and/or to/from a door.

Each of detection robot 60 and plate robot 88 has a respective tower 268, 270 supported by transverse rails 272 or 274 of carriage 260 or 264. Tower 268 can be driven horizontally along rails 272, indicated at 68 (see FIG. 7). Tower 270 can be driven horizontally along rails 274, indicated at 94. A detection module 164 of detection robot 60 can be driven vertically along tower 268, indicated at 276. Similarly, a grasping head 278 of plate robot 88 can be driven vertically along tower 270, indicated at 280. Grasping head 278 has a pair of jaws 282 to grip and/or support each microplate, such as gripped microplate 284, during transport thereof.

FIGS. 5 and 6 also show exemplary features of fluid handling station 72 in more detail. Plate dock 74 may have seating positions for two or more plates (see FIG. 6). For example, in the depicted embodiment, a microplate 58 and a master plate 292 (with deep wells) are seated in plate dock 74. Master plate 292 may be replaced in plate dock 74 with one of assay plates 86 when fluid handling station 72 is tasked with setting up an assay. A box of tips 82*c* has been moved into plate dock 74 from a stack of boxes containing new tips 82*a*. Tips 82*c* are located intermediate plates 58, 292 for utilization by pipette 78.

Pipette 78 can be driven along three orthogonal axes via a nested series of three carriages (and associated motors) that move along respective sets of rails (see FIGS. 5 and 6). A z-carriage 294 travels along rails 296, indicated by an arrow at 298, to raise and lower the working end of pipette 78 (see FIG. 5). An x-carriage 300 travels along rails 302, indicated by an arrow at 304, to move pipette 78 horizontally along an x-axis. A y-carriage 306 travels along rails 308, indicated by an arrow at 310, to move pipette 78 horizontally along a y-axis.

Figure 8:
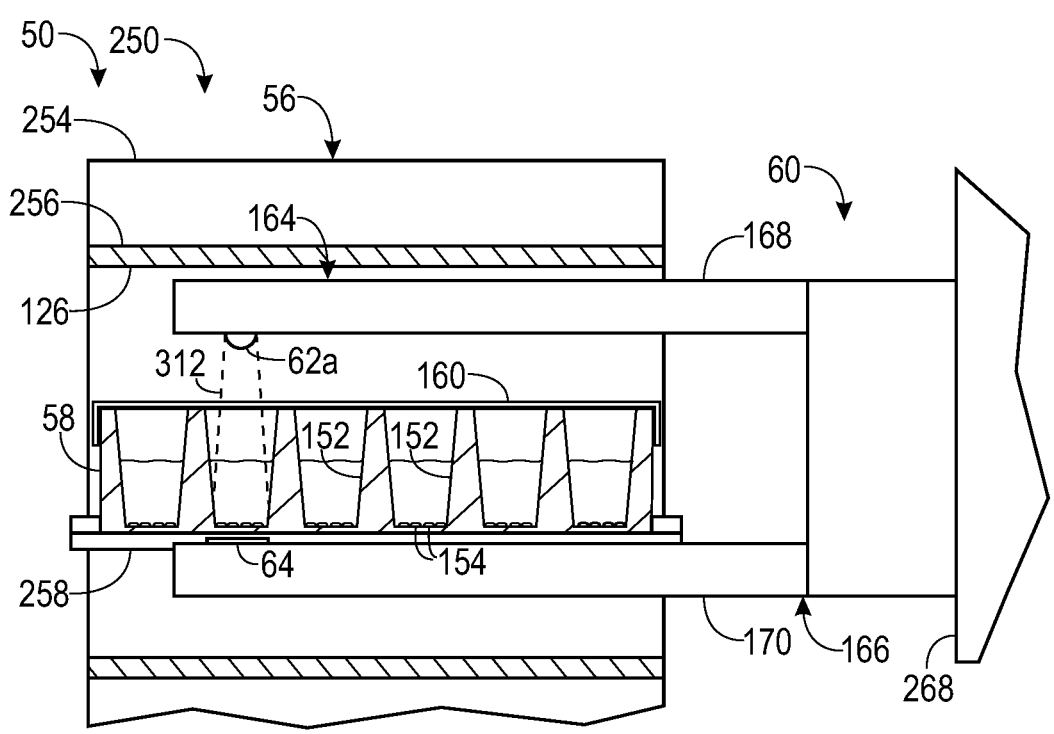
FIG. 8 is a fragmentary, sectional view of the operatively-loaded incubator of FIG. 5, taken generally along line 8-8 of FIG. 6.

FIGS. 7 and 8 show exemplary features of detection robot 60 in more detail. Arms 168, 170 of detection module 164 are positioned respectively above and below a microplate 58. A trans-illumination light source 62*a* and an image sensor 64 are aligned with one of wells 152 of microplate 58. Light source 62*a* is illuminating cells 154 through a lid 160 of microplate 58 with a light beam 312. Image sensor 64 is positioned very close to the bottom of well 152, without an intervening lens, for lensless imaging of cells 154.

Example 2

Selected Embodiments

This example describes selected systems and methods of the present disclosure as a series of indexed paragraphs.

Paragraph A1. An incubation system for automated cell culture and/or testing, comprising: (i) a housing forming a chamber; (ii) a rack defining storage positions to support an array of sample holders (such as microplates) inside the chamber; (iii) a detection robot to capture one or more images of cells contained by one or more wells (e.g., each well) of each sample holder while the sample holder remains at one of the storage positions of the rack; (iv) a fluid handling station configured to add fluid to, and/or remove fluid from, one or more wells (e.g., each well) of each of the sample holders inside the housing; (v) at least one plate robot to move sample holders between the rack and the fluid handling station; and (vi) a computer to control operation of the detection robot, the fluid handling station, and the at least one plate robot.

Paragraph A2. The incubation system of paragraph A1, wherein the detection robot is configured to capture the images by lensless imaging.

Paragraph A3. The incubation system of paragraph A1 or A2, wherein the detection robot is configured to lenslessly capture holograms representing cells located in one or more wells of each sample holder, and wherein the computer is configured to reconstruct one or more images of the cells located in the one or more wells using the captured holograms.

Paragraph A4. The incubation system of paragraph A3, wherein the detection robot is configured to illuminate cells located in one or more wells of each sample holder with light that is at least partially coherent.

Paragraph A5. The incubation system of paragraph A3 or A4, wherein the detection robot is configured to illuminate cells with light that has propagated through a waveguide, and wherein an outlet of the waveguide (e.g., a fiber optic or liquid light guide) is configured to travel with the detection robot to each of the storage positions of the rack.

Paragraph A6. The incubation system of paragraph A5, wherein the outlet of the waveguide has a diameter of less than about 100 micrometers.

Paragraph A7. The incubation system of paragraph A5 or A6, wherein a light source is optically coupled to the waveguide such that light generated by the light source is transmitted from the outlet of the waveguide.

Paragraph A8. The incubation system of paragraph A7, wherein the light source is supported by the detection robot and is configured to travel with the detection robot to each of the storage positions.

Paragraph A9. The incubation system of paragraph A7, wherein the light source is configured to be stationary while the detection robot travels to the each of the storage positions.

Paragraph A10. The incubation system of any of paragraphs A1 to A9, wherein the detection robot is configured to illuminate cells in one or more wells of each sample holder with light generated by a point source.

Paragraph A11. The incubation system of any of paragraphs A1 to A10, wherein the detection robot is configured to illuminate cells of one or more wells of each sample holder with light generated by a light-emitting diode, a laser diode, or a diode-pumped solid-state laser.

Paragraph A12. The incubation system of any of paragraphs A1 to A11, wherein the detection robot includes an image sensor, and wherein the image sensor includes a CCD sensor or a CMOS sensor.

Paragraph A13. The incubation system of any of paragraphs A1 to A12, wherein the fluid handling station is configured to dispense fluid to, and remove fluid from, wells of the sample holders inside the chamber.

Paragraph A14. The incubation system of paragraph A13, wherein the chamber is an incubation chamber, wherein the housing forms an entry/exit chamber sized to contain one or more of the sample holders, wherein the incubation chamber communicates with the entry/exit chamber via an inner door, and wherein the entry/exit chamber is accessible from outside the housing via an outer door.

Paragraph A15. The incubation system of any of paragraphs A1 to A14, wherein the fluid handling station includes a pipette and one or more storage locations for containers holding removable tips for the pipette.

Paragraph A16. The incubation system of paragraph A15, wherein the fluid handling station includes a first stack position for containers holding new tips for the pipette and a second stack position for containers holding tips already used by the pipette.

Paragraph A17. The incubation system of any of paragraphs A1 to A16, wherein the fluid handling station includes receiving sites for one of the sample holders and an assay plate and/or a master plate.

Paragraph A18. The incubation system of any of paragraphs A1 to A17, wherein the fluid handling station includes a lid robot to remove and replace lids of the sample holders.

Paragraph A19. The incubation system of any of paragraphs A1 to A18, wherein the at least one plate robot includes a first plate robot and a second plate robot, wherein the housing has a door bounding part of the chamber, wherein the first plate robot is configured to transport sample holders from the rack to a position near or at the door, and wherein the second plate robot is configured to transport sample holders from the position near or at the door to the fluid handling station, which is outside the chamber.

Paragraph A20. The incubation system of paragraph A19, wherein the housing has an inner door and an outer door, and wherein the first and second plate robots are configured to cooperatively move each sample holder from the rack to the fluid handling station through the inner door and the outer door.

Paragraph A21. The incubation system of paragraph A20, wherein the chamber is a first chamber, and wherein the fluid handling station is located in a second chamber that communicates with the first chamber via the inner and outer doors.

Paragraph A22. The incubation system of any of paragraphs A1 to A21, wherein the rack has a first side opposite a second side, wherein a plate robot of the at least one plate robot is configured to move sample holders into and out of the storage positions via the first side of the rack, and wherein the detection robot is configured to operatively access sample holders in the storage positions via the second side of the rack.

Paragraph A23. The incubation system of paragraph A22, wherein the storage positions of the rack are arranged in horizontal rows and vertical columns, and wherein the plate robot and the detection robot are collectively capable of operatively accessing a pair of storage positions within the same horizontal row simultaneously and of operatively accessing a pair of storage positions within the same vertical column simultaneously.

Paragraph A24. The incubation system of any of paragraphs A1 to A23, wherein the rack includes a plurality of heaters operatively associated with the storage positions and configured to heat lids of sample holders in the storage positions to reduce condensation prior to image capture with the detection robot.

Paragraph A25. The incubation system of paragraph A24, wherein subsets of the heaters are controllable independently from one another with the computer.

Paragraph A26. The incubation system of paragraph A24 or A25, wherein a different heater of the plurality of heaters is operatively associated with each storage position of the rack and is controllable with the computer independently of each other heater of the plurality of heaters.

Paragraph A27. The incubation system of any of paragraphs A1 to A26, further comprising a thermal control system configured to maintain the chamber at a predefined incubation temperature above room temperature.

Paragraph A28. The incubation system of any of paragraphs A1 to A27, further comprising a source of carbon dioxide connected to the chamber.

Paragraph A29. The incubation system of any of paragraphs A1 to A28, further comprising a source of water configured to humidify the chamber.

Paragraph A30. The incubation system of any of paragraphs A1 to A29, wherein the storage positions of the rack are arranged in horizontal rows and vertical columns, and wherein each horizontal row and each vertical column has at least two, three, or more of the storage positions.

Paragraph A31. The incubation system of any of paragraphs A1 to A30, further comprising a detection station configured to detect light from one or more wells (e.g., each well) of each sample holder, wherein the at least one plate robot is configured to transport each of the sample holders between the rack and the detection station.

Paragraph A32. The incubation system of paragraph A31, wherein the detection station is configured to detect photoluminescence from one or more wells (e.g., each well) of each sample holder.

Paragraph A33. The incubation system of paragraph A31 or A32, wherein the detection station includes a lid robot to remove and replace lids of the sample holders, and wherein the detection station includes a waveguide, such as a fiber optic, configured to be placed into each well of each sample holder.

Paragraph A34. The incubation system of any of paragraphs A1 to A33, wherein the computer is configured to send captured images of cells in wells of the sample holders to a remote user via the Internet.

Paragraph A35. The incubation system of paragraph A34, wherein the computer is configured to receive instructions from the remote user via the Internet, and wherein the instructions tell the computer whether and/or how to process cultures of the cells depicted in the sent images.

Paragraph A36. The incubation system of paragraph A34 or A35, wherein the computer is configured to receive instructions from the remote user via the Internet for processing cultures of cells depicted in the sent images.

Paragraph A37. The incubation system of any of paragraphs A1 to A36, wherein the computer is configured to determine whether and/or when to add fluid to and/or remove fluid from one or more wells of each sample holder at the fluid handling station based on the captured images.

Paragraph A38. The incubation system of paragraph A37, wherein the computer is configured to determine a characteristic, such as a density/confluence/cell count, of cells contained by one or more wells of each sample holder from one or more images captured by the detection robot, and to decide whether and/or when to add fluid to and/or remove fluid from such wells based on the characteristic.

Paragraph A39. The incubation system of any of paragraphs A1 to A38, further comprising a sample holder including a pH sensor device and/or an oxygen sensor device disposed in one or more wells of the sample holder, wherein the incubation system includes an optical sensor configured to detect photoluminescence from the sensor device(s).

Paragraph A40. The incubation system of paragraph A39, wherein the detection robot includes the optical sensor and is configured to illuminate the sensor device to induce the photoluminescence.

Paragraph A41. The incubation system of any of paragraphs A1 to A40 configured to perform any method or method steps of any of paragraphs B1 to B25.

Paragraph B1. A method of automated cell culture and/or testing, the method comprising: (i) capturing one or more images of cells contained in one or more wells of each sample holder of a plurality of sample holders, the plurality of sample holders being stored at storage positions defined by a rack inside an incubator, wherein the sample holder remains in its storage position in the rack as the images are captured for the sample holder; (ii) moving the sample holder from the rack to a fluid handling station inside the incubator using a plate robot; and (iii) removing fluid from, and/or adding fluid to, at least one well of the sample holder at the fluid handling station.

Paragraph B2. The method of paragraph B1, wherein capturing one or more images is performed lenslessly.

Paragraph B3. The method of paragraph B1 or B2, wherein capturing one or more images includes illuminating cells with at least partially coherent light.

Paragraph B4. The method of any of paragraphs B1 to B3, wherein illuminating cells includes propagating light for illumination through a waveguide upstream of the cells.

Paragraph B5. The method of paragraph B3, wherein capturing one or more images includes capturing two or more images representing at least similar fields of view of the illuminated cells but (i) different z-positions of an image sensor that captures the two or more images, (ii) different angles of incidence of illumination, (iii) different wavelengths of illumination, and/or (iv) sub-pixel shifts in lateral position of the image sensor and/or a light source.

Paragraph B6. The method of any of paragraphs B1 to B5, wherein capturing one or more images includes capturing holograms.

Paragraph B7. The method of paragraph B6, further comprising reconstructing images of cells by digitally processing data from the captured holograms.

Paragraph B8. The method of paragraph B7, wherein reconstructing images includes retrieving phase from the captured holograms.

Paragraph B9. The method of any of paragraphs B1 to B8, wherein capturing one or more images includes capturing one or more images for each well of a plurality of wells of the sample holder, and processing the one or more images to obtain a value corresponding to a confluence/density/cell count of cells in the well, wherein the step of moving is performed for the sample holder if the value(s) for one or more wells meets one or more predefined criteria.

Paragraph B10. The method of any of paragraphs B1 to B9, further comprising sending one or more images of cells resulting from the step of capturing one or more images to a user; receiving a command from the user to perform the step of moving; and removing and/or adding fluid at the fluid handling station in response to the command.

Paragraph B11. The method of paragraph B10, wherein capturing one or more images and moving are controlled by a local computer, and wherein the steps of sending and receiving are performed by communication between a remote computing device operated by the user and in communication with the local computer via the Internet.

Paragraph B12. The method of paragraph B10 or B11, further comprising receiving instructions from the user for removing and/or adding fluid.

Paragraph B13. The method of any of paragraphs B10 to B12, wherein capturing one or more images and moving are controlled by a local computer, the method further comprising displaying the one or more images to the user using a monitor of the local computer.

Paragraph B14. The method of any of paragraphs B1 to B13, wherein two or more of the sample holders are aligned vertically with one another in the rack.

Paragraph B15. The method of any of paragraphs B1 to B14, further comprising applying heat locally and/or temporarily within the incubator to each sample holder before capturing one or more images for the sample holder, to reduce condensation on a lid thereof.

Paragraph B16. The method of paragraph B15, wherein applying heat is performed with a dedicated heater for each sample holder.

Paragraph B17. The method of paragraph B15 or B16, wherein applying heat is performed with a plurality of heaters each located above a different sample holder in the rack.

Paragraph B18. The method of any of paragraphs B15 to B17, wherein applying heat is performed for a predefined time period before one or more images are captured for the sample holder.

Paragraph B19. The method of any of paragraphs B1 to B18, wherein removing and/or adding fluid includes transferring fluid from the at least one well to a well of an assay plate.

Paragraph B20. The method of paragraph B19, further comprising performing an assay in the well of the assay plate.

Paragraph B21. The method of paragraph B20, wherein the assay includes an ELISA assay.

Paragraph B22. The method of paragraph B20 or B21, further comprising reading a result from the well of the assay plate outside the incubator.

Paragraph B23. The method of any of paragraphs B19 to B22, wherein capturing one or more images is performed in a main chamber of the incubator, further comprising a step of transporting the assay plate from the main chamber to an entry/exit chamber of the incubator using a plate robot.

Paragraph B24. The method of any of paragraphs B1 to B23, wherein removing and/or adding fluid includes removing old culture medium from the at least one well, and adding new culture medium to the at least one well, to feed cells in the at least one well.

Paragraph B25. The method of any of paragraphs B1 to B24, wherein removing and/or adding fluid includes a step of adding a test compound contained in fluid to the at least one well.

Paragraph B26. The method of any of paragraphs B1 to B25, performed with any of the systems or system features recited in paragraphs A1 to A40.

The term "exemplary" as used in the present disclosure, means "illustrative" or "serving as an example." Similarly, the term "exemplify" means "illustrate by giving an example." Neither term implies desirability nor superiority.

The disclosure set forth above may encompass multiple distinct inventions with independent utility. Although each of these inventions has been disclosed in its preferred form(s), the specific embodiments thereof as disclosed and illustrated herein are not to be considered in a limiting sense, because numerous variations are possible. The subject matter of the inventions includes all novel and nonobvious combinations and subcombinations of the various elements, features, functions, and/or properties disclosed herein. The following claims particularly point out certain combinations and subcombinations regarded as novel and nonobvious. Inventions embodied in other combinations and subcombinations of features, functions, elements, and/or properties may be claimed in applications claiming priority from this or a related application. Such claims, whether directed to a different invention or to the same invention, and whether broader, narrower, equal, or different in scope to the original claims, also are regarded as included within the subject matter of the inventions of the present disclosure. Further, ordinal indicators, such as first, second, or third, for identified elements are used to distinguish between the elements, and do not indicate a particular position or order of such elements, unless otherwise specifically stated.

We claim:

1. An incubation system for automated cell culture and/or testing, the system comprising:
    a housing forming a chamber;
    a climate control system for controlling at least one of a temperature and a humidity of the chamber;
    a rack defining a plurality of storage positions to support an array of sample holders inside the chamber, each sample holder having a plurality of wells;
    a plurality of local heaters, wherein each of the plurality of local heaters are associated with individual storage positions of each of the plurality of storage positions;
    a detection robot movable between each of the plurality of storage positions to capture a corresponding plurality of images of cells contained by the plurality of wells of at least one sample holder of the array of sample holders while the at least one sample holder remains at one of the storage positions of the rack, wherein the detection robot is movable along three orthogonal axes, to reach every well of each sample holder supported by the rack;
    a fluid handling station comprising a pump configured to add fluid to, and/or remove fluid from, each of the wells of each of the sample holders inside the housing;
    at least one plate robot to move sample holders between the rack and the fluid handling station; and
    a computer to control operation of the climate control system, each of the plurality of local heaters, the detection robot, the fluid handling station, and the at least one plate robot;
    and wherein the plurality of storage positions and the corresponding plurality of local heaters are separated from one another with sufficient clearance for access by the detection robot.

2. The incubation system of claim 1, wherein the detection robot comprises an image sensor that is configured to capture images by lensless imaging.

3. The incubation system of claim 2, wherein the detection robot is configured to lenslessly capture one or more holograms representing cells located in one or more wells of each sample holder, and wherein the computer is configured to reconstruct images of the cells located in the wells using the captured holograms.

4. The incubation system of claim 3, wherein the detection robot further comprises a waveguide that is configured to illuminate cells with light that has propagated through the waveguide, and wherein an outlet of the waveguide is configured to travel with the detection robot to each of the storage positions of the rack.

5. The incubation system of claim 1, wherein the fluid handling station is configured to dispense fluid to, and remove fluid from, wells of the sample holders inside the chamber.

6. The incubation system of claim 1, further comprising an inner door and an outer door, wherein the chamber is an incubation chamber, wherein the housing forms an entry/exit chamber sized to contain one or more sample holders, wherein the incubation chamber communicates with the entry/exit chamber via the inner door, and wherein the entry/exit chamber is accessible from outside the housing via the outer door.

7. The incubation system of claim 1, wherein the fluid handling station includes a pipette and one or more storage locations for containers holding removable tips for the pipette.

8. The incubation system of claim 7, wherein the fluid handling station includes a first stack position for containers holding new tips for the pipette and a second stack position for containers holding tips already used by the pipette.

9. The incubation system of claim 1, wherein the fluid handling station includes receiving sites for at least one of the sample holders and an assay plate and/or a master plate, wherein the assay plate and master plate are different than the at least one of the sample holders.

10. The incubation system of claim 1, wherein the rack has a first side opposite a second side, wherein a plate robot of the at least one plate robot is configured to move sample holders into and out of the storage positions via the first side of the rack, and wherein the detection robot is configured to operatively access sample holders in the storage positions via the second side of the rack.

11. The incubation system of claim 1, wherein each of the plurality of the local heaters operatively associated with the storage positions of the rack are configured to heat lids of sample holders in the storage positions to reduce condensation prior to image capture with the detection robot.

12. The incubation system of claim 1, wherein the computer is configured to send one or more of the captured images via the Internet to a remote user, and wherein the computer is configured to receive instructions from the remote user on whether and/or how to process cultures of cells depicted in the sent images.

13. The incubation system of claim 1, wherein the computer is configured to determine whether and/or when to add fluid to and/or remove fluid from one or more wells of each sample holder at the fluid handling station based on images captured by the detection robot.

14. The incubation system of claim 13, wherein the computer is configured to determine a characteristic of cells contained by one more wells of each sample holder from images captured by the detection robot, and to decide whether and/or when to add fluid to and/or remove fluid from such wells based on the characteristic.

15. The incubation system of claim 1, further comprising a sample holder comprising a sensor device comprising at least one of a pH sensor device and/or an oxygen sensor device disposed in one or more wells of the sample holder, wherein the incubation system includes an optical sensor configured to detect photoluminescence from the sensor device.

* * * * *